US012611157B2

(12) United States Patent　　(10) Patent No.:　US 12,611,157 B2

Kawamura　　(45) Date of Patent:　Apr. 28, 2026

(54) RADIATION IMAGE PROCESSING DEVICE, RADIATION IMAGE PROCESSING METHOD, AND RADIATION IMAGE PROCESSING PROGRAM

(71) Applicant: FUJIFILM Corporation, Tokyo (JP)

(72) Inventor: Takahiro Kawamura, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 610 days.

(21) Appl. No.: 18/047,232

(22) Filed: Oct. 17, 2022

(65) Prior Publication Data

US 2023/0134187 A1　　May 4, 2023

(30) Foreign Application Priority Data

Nov. 2, 2021　(JP) ................................. 2021-179655

(51) Int. Cl.
A61B 6/00　　　(2024.01)

(52) U.S. Cl.
CPC ............ A61B 6/5282 (2013.01); A61B 6/481 (2013.01); A61B 6/482 (2013.01)

(58) Field of Classification Search
CPC ......... G06T 7/0012; G06T 2207/10116; G06T 2210/41; G06T 2207/30004;
(Continued)

(56) References Cited

U.S. PATENT DOCUMENTS 10,136,873 B2 * 11/2018 Kawamura .......... A61B 6/5282
11,730,388 B2 * 8/2023 Laub ................... G01R 33/5608
　　　　　　　　　　　　　　　　　　324/309

(Continued)

FOREIGN PATENT DOCUMENTS

EP　　　　2998729 A1 *　3/2016　.......... A61B 6/5205
JP　　2004-000609 A　　1/2004
(Continued)

OTHER PUBLICATIONS

An Office Action; "Notice of Reasons for Refusal," mailed by the Japanese Patent Office on Jun. 3, 2025, which corresponds to Japanese Patent Application No. 2021-179655 and is related to U.S. Appl. No. 18/047,232; with English language translation.

*Primary Examiner* — Andrew W Bee
*Assistant Examiner* — Rebecca Colette Williams
(74) *Attorney, Agent, or Firm* — Studebaker Brackett PLLC

(57)　　　　　ABSTRACT

A processor acquires two radiation images having a contrast based on a first characteristic related to a first imaging apparatus, derives a body thickness distribution of a subject based on at least one of the two radiation images, removes a scattered ray component from the two radiation images based on the first characteristic, derives a first bone part image and a first soft part image representing a bone tissue and a soft tissue of the subject, respectively, from the two radiation images, converts the first bone part image and the first soft part image into a second bone part image and a second soft part image having a contrast based on a second characteristic related to a second imaging apparatus, based on the first characteristic, the second characteristic, and the body thickness distribution, and derives a processed radiation image having the contrast based on the second characteristic by adding the second bone part image and the second soft part image.

6 Claims, 8 Drawing Sheets

(58) Field of Classification Search
CPC . G06T 2207/30008; G06T 2207/30096; G06T
7/0016; G06T 5/50; G06T 2211/452;
G06T 2207/10072; G06T 7/0014; G06T
2207/10081; G06T 2207/10088; G06T
11/005; G06T 2207/30048; G06T
2207/30061; G06T 2207/30101; G06T
2207/30068; G06T 2207/30016; G06T
2207/30056; G06T 2207/30081; G06T
2207/30041; G06T 2207/20221; G06T
2207/10104; G06T 11/003; A61B 6/482;
A61B 6/4266
See application file for complete search history.

(56)  References Cited

U.S. PATENT DOCUMENTS

| | | | |
|---|---|---|---|
| 2003/0215119 A1 | 11/2003 | Uppaluri et al. | |
| 2014/0105479 A1* | 4/2014 | Tsai | G06T 7/0012 |
| | | | 378/62 |
| 2016/0000396 A1 | 1/2016 | Taguchi et al. | |
| 2016/0140720 A1 | 5/2016 | Naito | |
| 2017/0055933 A1* | 3/2017 | Kawamura | G06T 11/005 |
| 2018/0068422 A1* | 3/2018 | Kawamura | G06T 5/70 |
| 2018/0108118 A1* | 4/2018 | Takahashi | A61B 6/5235 |
| 2018/0122094 A1* | 5/2018 | Naito | A61B 6/5282 |
| 2020/0305829 A1* | 10/2020 | Takahashi | A61B 6/465 |

FOREIGN PATENT DOCUMENTS

| | | | | |
|---|---|---|---|---|
| JP | 2015-043959 A | 3/2015 | | |
| JP | 2016-026556 A | 2/2016 | | |
| JP | 2018038638 A * | 3/2018 | | G06T 11/00 |
| JP | 2019208927 A * | 12/2019 | | |
| WO | 2005/111718 A1 | 11/2005 | | |
| WO | WO-2020250900 A1 * | 12/2020 | | G01T 1/36 |
| WO | WO-2021059668 A1 * | 4/2021 | | A61B 6/12 |

* cited by examiner

THICKNESS OF STANDARD OBJECT [cm]

THICKNESS OF STANDARD OBJECT [cm]

RADIATION IMAGE PROCESSING DEVICE, RADIATION IMAGE PROCESSING METHOD, AND RADIATION IMAGE PROCESSING PROGRAM

CROSS REFERENCE TO RELATED APPLICATIONS

The present application claims priority under 35 U.S.C. § 119 to Japanese Patent Application No. 2021-179655 filed on Nov. 2, 2021. The above application is hereby expressly incorporated by reference, in its entirety, into the present application.

BACKGROUND

Technical Field

The present disclosure relates to a radiation image processing device, a radiation image processing method, and a radiation image processing program.

Related Art

In the related art, in a case of making a diagnosis using a radiation image, comparative interpretation using past radiation images of a patient has been performed. For example, for the radiation image of the patient, it is possible to check a degree of progression of a lesion or detect an abnormality at an early stage by displaying the radiation image acquired in the latest examination and the radiation image acquired in the past examination and performing the comparative interpretation.

In addition, a computer aided diagnostic imaging system (computer aided diagnosis: CAD, hereinafter referred to as CAD) that automatically detects a structure, such as an abnormal shadow in the image and highlights and displays the detected structure has also been proposed.

In addition, in a case in which the radiation image of a subject is captured, particularly in a case in which a thickness of the subject is large, there is a problem that radiation is scattered in the subject to generate scattered rays, and a contrast of the acquired radiation image is lowered by the generated scattered rays. Therefore, scattered ray removal processing of removing a scattered ray component included in the radiation image is performed (for example, see JP2015-043959A). Specifically, the scattered ray removal processing is performed by deriving the scattered ray component of the radiation image based on a radiation attenuation coefficient of the subject, and subtracting the derived scattered ray component from the radiation image.

In order to perform the comparative interpretation described above with high accuracy, it is important to reproduce the contrasts of two radiation images to be compared. The contrast of the radiation image varies depending on a characteristic of an imaging apparatus, such as energy of radiation emitted to the subject, a top plate of an imaging table on which the subject is placed, or a scattered ray removal grid for removing the scattered ray component included in the radiation transmitted through the subject. Therefore, in a case in which two radiation images for the comparative interpretation are acquired under the same imaging condition with the same imaging apparatus, the contrasts of the two radiation images match, so that the comparative interpretation can be performed with high accuracy.

However, in a case in which the two radiation images for the comparative interpretation are acquired by different imaging apparatuses, the contrasts of the two radiation images are different. In addition, in a case in which the imaging condition (a tube voltage of a radiation source, an imaging distance, a tube current, or the like) at the time of imaging differs, the contrasts of the two radiation images will differ. In addition, the contrast of the radiation image is also changed depending on the scattered ray included in the radiation image.

As described above, in a case in which the two radiation images have different contrasts, the comparative interpretation cannot be performed with high accuracy. An experienced doctor can perform the interpretation in consideration of a difference in the contrast of the radiation image due to a difference in the apparatus, but there is a heavy burden on the doctor. In addition, in a case in which the abnormal shadow is detected from the radiation image by using the CAD described above, in a case in which the contrast of the radiation image input to the CAD differs, there is a probability that the detection accuracy of the abnormal shadow will be lowered.

SUMMARY OF THE INVENTION

The present disclosure has been made in view of the above circumstances, and is to make it possible to match the contrasts of two radiation images having different imaging conditions and different characteristics of an acquisition apparatus.

The present disclosure relates to a radiation image processing device comprising at least one processor, in which the processor acquires two radiation images having a contrast based on a first characteristic related to a first imaging apparatus, the two radiation images being acquired by imaging a subject including a soft part and a bone part with the first imaging apparatus using radiation having different energy distributions, derives a body thickness distribution of the subject based on at least one of the two radiation images, removes a scattered ray component, which is included in radiation transmitted through the subject and is scattered by the subject, from the two radiation images based on the first characteristic, derives a first bone part image representing a bone tissue of the subject and a first soft part image representing a soft tissue of the subject by performing weighting subtraction on the two radiation images from which the scattered ray component is removed, converts the first bone part image and the first soft part image into a second bone part image and a second soft part image having a contrast based on a second characteristic related to a second imaging apparatus different from the first imaging apparatus, based on the first characteristic, the second characteristic, and the body thickness distribution, and derives a processed radiation image having the contrast based on the second characteristic by adding the second bone part image and the second soft part image.

Note that, in the radiation image processing device according to the present disclosure, the processor may derive a scattered ray component in accordance with the second characteristic based on the second characteristic and the body thickness distribution, and may further derive the processed radiation image by using the derived scattered ray component.

In addition, in the radiation image processing device according to the present disclosure, the first characteristic may include energy of the radiation used in the first imaging apparatus, a radiation attenuation coefficient in accordance with the body thickness distribution for an object interposed between the subject and a radiation detector that detects the radiation transmitted through the subject in the first imaging apparatus, a ratio of the scattered ray component included in the radiation transmitted through the subject in accordance with the body thickness distribution, and a point spread function in accordance with the body thickness distribution, and the second characteristic may include energy of the radiation used in the second imaging apparatus, a radiation attenuation coefficient in accordance with the body thickness distribution for an object interposed between the subject and a radiation detector that detects the radiation transmitted through the subject in the second imaging apparatus, a ratio of the scattered ray component included in the radiation transmitted through the subject in accordance with the body thickness distribution, and a point spread function in accordance with the body thickness distribution.

In addition, in the radiation image processing device according to the present disclosure, the processor may display the processed radiation image and a radiation image of the subject acquired by the second imaging apparatus.

The present disclosure relates to a radiation image processing method comprising acquiring two radiation images having a contrast based on a first characteristic related to a first imaging apparatus, the two radiation images being acquired by imaging a subject including a soft part and a bone part with the first imaging apparatus using radiation having different energy distributions, deriving a body thickness distribution of the subject based on at least one of the two radiation images, removing a scattered ray component, which is included in radiation transmitted through the subject and is scattered by the subject, from the two radiation images based on the first characteristic, deriving a first bone part image representing a bone tissue of the subject and a first soft part image representing a soft tissue of the subject by performing weighting subtraction on the two radiation images from which the scattered ray component is removed, converting the first bone part image and the first soft part image into a second bone part image and a second soft part image having a contrast based on a second characteristic related to a second imaging apparatus different from the first imaging apparatus, based on the first characteristic, the second characteristic, and the body thickness distribution, and deriving a processed radiation image having the contrast based on the second characteristic by adding the second bone part image and the second soft part image.

Note that a program causing a computer to execute the radiation image processing method according to the present disclosure may be provided.

According to the present disclosure, it is possible to match the contrasts of two radiation images having different imaging conditions and different characteristics of an acquisition apparatus.

DETAILED DESCRIPTION

Figure 1:
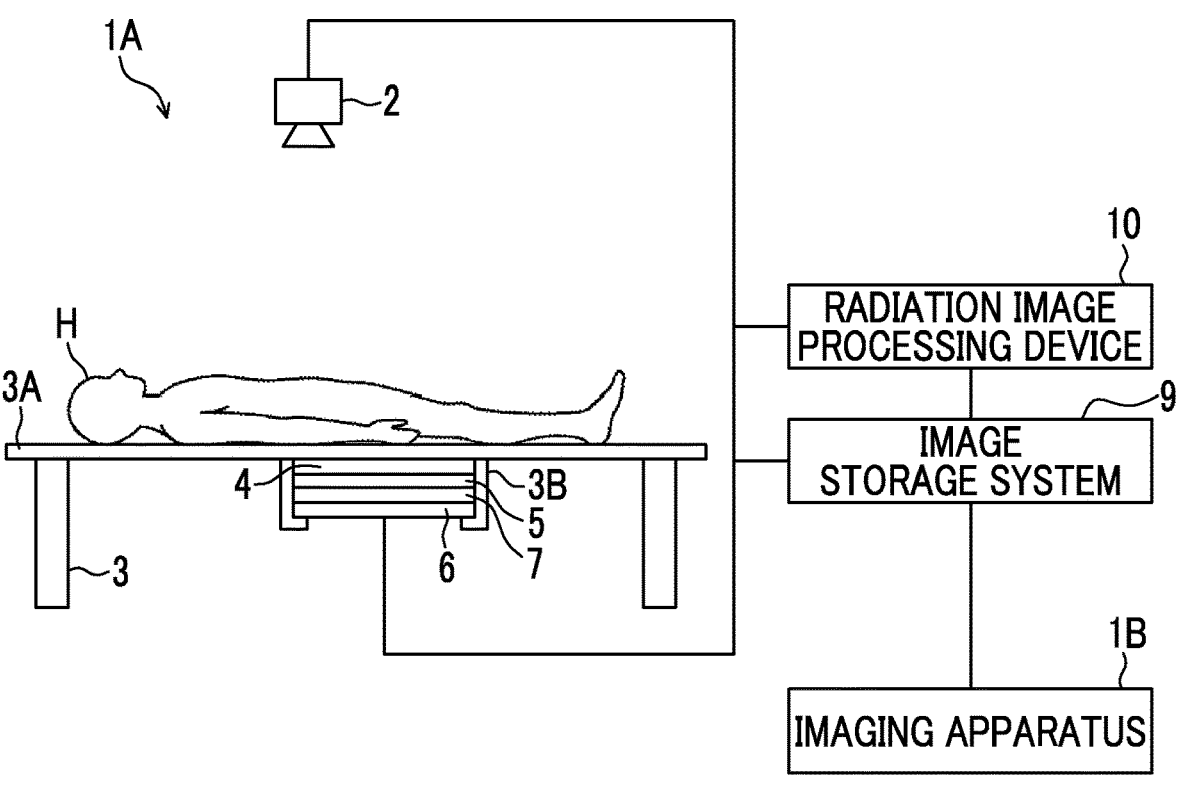
FIG. 1 is a schematic block diagram showing a configuration of a radiography system to which a radiation image processing device according to an embodiment of the present disclosure is applied.

Hereinafter, an embodiment of the present disclosure will be described with reference to the drawings. FIG. 1 is a schematic block diagram showing a configuration of a radiography system to which a radiation image processing device according to the embodiment of the present disclosure is applied. As shown in FIG. 1, the radiography system according to the present embodiment comprises an imaging apparatus 1A, an imaging apparatus 1B, an image storage system 9, and a radiation image processing device 10 according to the present embodiment. The imaging apparatus 1A, the imaging apparatus 1B, the image storage system 9, and the radiation image processing device 10 are connected to the image storage system 9 via a network (not shown).

The imaging apparatus 1A is an imaging apparatus that performs energy subtraction by a so-called one-shot method of converting radiation, such as X-rays, emitted from a radiation source 2 and transmitted through a subject H who lies on an imaging table 3 into energy and irradiating a first radiation detector 5 and a second radiation detector 6 with the converted radiation. At the time of imaging, as shown in FIG. 1, a scattered ray removal grid (hereinafter simply referred to as a grid) 4, the first radiation detector 5, a radiation energy conversion filter 7 made of a copper plate or the like, and the second radiation detector 6 are disposed in order from a side closest to the radiation source 2, and the radiation source 2 is driven. The first and second radiation detectors 5 and 6 are closely attached to the radiation energy conversion filter 7. Note that the grid 4, the first radiation detector 5, the radiation energy conversion filter 7, and the second radiation detector 6 are attachably and detachably attached below a top plate 3A of the imaging table 3 by an attachment portion 3B.

As a result, in the first radiation detector 5, a first radiation image G1 of the subject H by low-energy radiation also including so-called soft rays is acquired. In addition, in the second radiation detector 6, a second radiation image G2 of the subject H by high-energy radiation from which the soft rays are removed is acquired. The first and second radiation images G1 and G2 are input to the radiation image processing device 10.

The first and second radiation detectors 5 and 6 can perform recording and reading-out of the radiation image repeatedly. A so-called direct-type radiation detector that directly receives emission of the radiation and generates an electric charge may be used, or a so-called indirect-type radiation detector that converts the radiation into visible light and then converts the visible light into an electric charge signal may be used. In addition, as a method for reading out a radiation image signal, it is desirable to use a so-called thin film transistor (TFT) readout method in which the radiation image signal is read out by turning a TFT switch on and off, or a so-called optical readout method in which the radiation image signal is read out by emission of read out light. However, other methods may also be used without being limited to these methods.

Note that in the imaging apparatus 1A, only one radiation detector may be attached to the attachment portion 3B to image the subject H.

The grid 4 is configured by lead that does not transmit the radiation and an interspace material, such as aluminum or fiber that easily transmit the radiation which are disposed alternately with a fine grid density of about 4.0 lines/mm. By using the grid 4, a scattered ray component of the radiation transmitted through the subject H can be removed, but it cannot be completely removed. Therefore, the first and second radiation images G1 and G2 also include a primary ray component of the radiation transmitted through the subject H as well as the scattered ray component.

The primary ray component is a signal component having a pixel value represented by the radiation that reaches the radiation detector without being scattered by the subject H in the radiation that is transmitted through the subject H. On the other hand, the scattered ray component is a signal component having a pixel value represented by the radiation that reaches the radiation detector by being scattered by the subject H in the radiation that is transmitted through the subject H.

Note that since the imaging apparatus 1B has the same configuration as the imaging apparatus 1A, the detailed description thereof will be omitted here. Note that, in the imaging apparatus 1A and the imaging apparatus 1B, the materials and thicknesses of the top plate used, and the characteristics of the grid used are different.

The image storage system 9 is a system that stores image data of the radiation image acquired by the imaging apparatuses 1A and 1B. For example, the image storage system 9 stores a plurality of radiation images of the same patient having different imaging dates and times. The image storage system 9 extracts an image corresponding to a request from the radiation image processing device 10 from the stored radiation image and transmits the extracted image to a request source device. Specific examples of the image storage system 9 include picture archiving and communication systems (PACS).

Here, in the present embodiment, the radiation image acquired in the past examination of the patient who is the subject H is stored in the image storage system 9. In addition, the radiation image of the past examination (hereinafter referred to as past radiation image) is acquired by the imaging apparatus 1B. In the radiation image processing device 10 according to the present embodiment, the past radiation image of the patient is acquired from the image storage system 9, and the comparative interpretation of the radiation image acquired by the latest examination and the past radiation image is performed.

Figure 2:
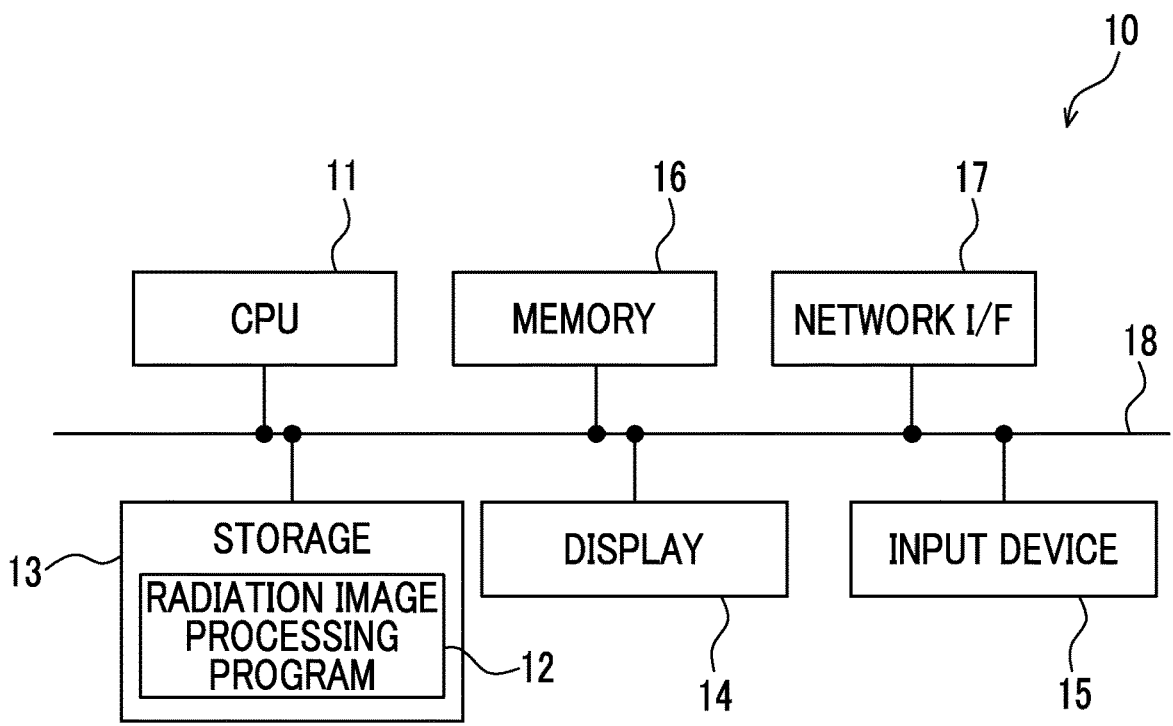
FIG. 2 is a diagram showing a schematic configuration of the radiation image processing device according to the embodiment of the present disclosure.

Then, the radiation image processing device according to the present embodiment will be described. First, with reference to FIG. 2, a hardware configuration of the radiation image processing device according to the present embodiment will be described. As shown in FIG. 2, the radiation image processing device 10 is a computer, such as a workstation, a server computer, and a personal computer, and comprises a central processing unit (CPU) 11, a non-volatile storage 13, and a memory 16 as a transitory storage region. In addition, the radiation image processing device 10 comprises a display 14, such as a liquid crystal display, an input device 15, such as a keyboard and a mouse, and a network interface (I/F) 17 connected to a network (not shown). The CPU 11, the storage 13, the display 14, the input device 15, the memory 16, and the network I/F 17 are connected to a bus 18. Note that the CPU 11 is an example of a processor according to the present disclosure.

The storage 13 is realized by a hard disk drive (HDD), a solid state drive (SSD), a flash memory, and the like. A radiation image processing program 12 installed in the radiation image processing device 10 is stored in the storage 13 as a storage medium. The CPU 11 reads out the radiation image processing program 12 from the storage 13, expands the read out radiation image processing program 12 to the memory 16, and executes the expanded radiation image processing program 12.

Note that the radiation image processing program 12 is stored in a storage device of the server computer connected to the network or in a network storage in a state of being accessible from the outside, and is downloaded and installed in the computer that configures the radiation image processing device 10 in response to the request. Alternatively, the radiation image processing program 12 is distributed in a state of being recorded on a recording medium, such as a digital versatile disc (DVD) or a compact disc read only memory (CD-ROM), and is installed in the computer that configures the radiation image processing device 10 from the recording medium.

Figure 3:
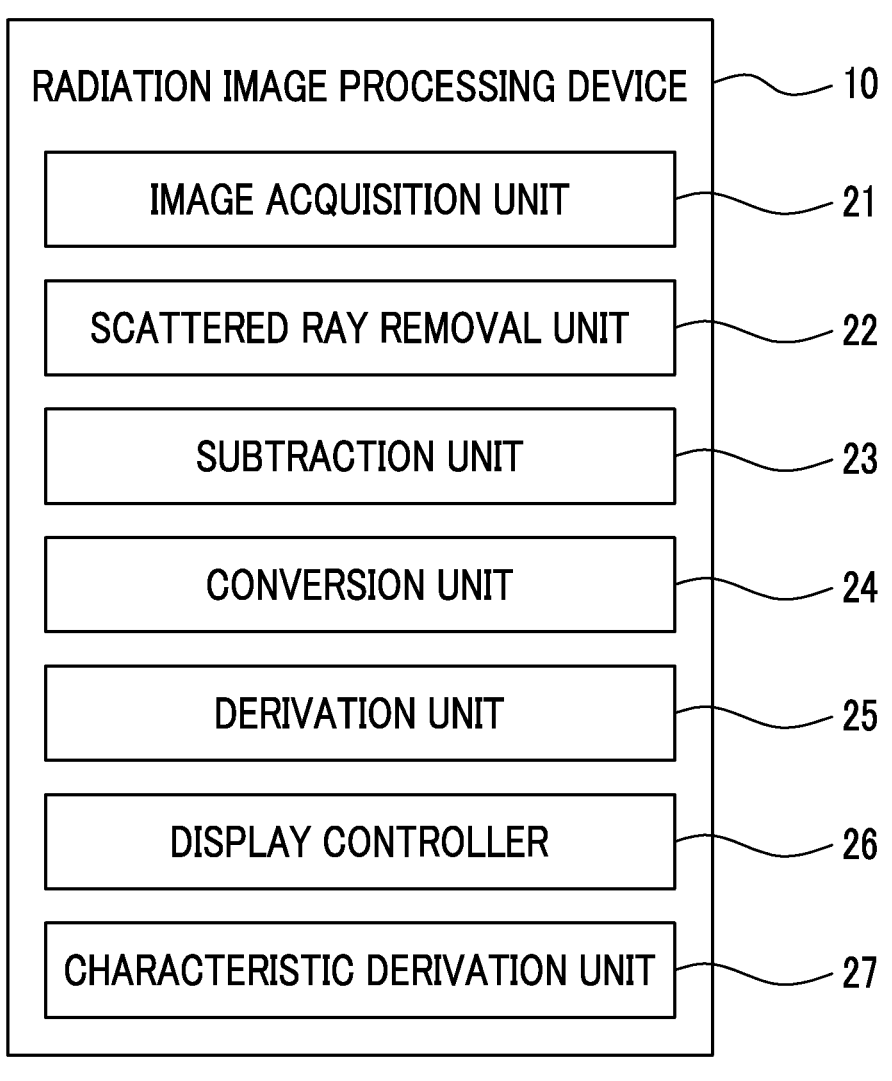
FIG. 3 is a diagram showing a functional configuration of the radiation image processing device according to the embodiment of the present disclosure.

Then, a functional configuration of the radiation image processing device according to the present embodiment will be described. FIG. 3 is a diagram showing the functional configuration of the radiation image processing device according to the present embodiment.

As shown in FIG. 3, the radiation image processing device 10 comprises an image acquisition unit 21, a scattered ray removal unit 22, a subtraction unit 23, a conversion unit 24, a derivation unit 25, a display controller 26, and a characteristic derivation unit 27. Moreover, by executing the radiation image processing program 12, the CPU 11 functions as the image acquisition unit 21, the scattered ray removal unit 22, the subtraction unit 23, the conversion unit 24, a derivation unit 25, the display controller 26, and the characteristic derivation unit 27.

The image acquisition unit 21 acquires the first radiation image G1 and the second radiation image G2 of the subject H from the first and second radiation detectors 5 and 6 by causing the imaging apparatus 1A to perform the energy subtraction imaging of the subject H. In a case in which the first radiation image G1 and the second radiation image G2 are acquired, an imaging conditions, such as an imaging dose, a radiation quality, a tube voltage (kV), a source image receptor distance (SID) which is a distance between the radiation source 2 and surfaces of the first and second radiation detectors 5 and 6, a source object distance (SOD) which is a distance between the radiation source 2 and a surface of the subject H, and the presence or absence of a scattered ray removal grid are set. The imaging conditions need only be set by input from the input device 15 by an operator.

The SOD and the SID are used to calculate a body thickness distribution as described below. It is preferable that the SOD be acquired by, for example, a time of flight (TOF) camera. It is preferable that the SID be acquired by, for example, a potentiometer, an ultrasound range finder, a laser range finder, or the like.

The imaging conditions need only be set by input from the input device 15 by the operator. The set imaging condition is stored in the storage 13. The first and second radiation images G1 and G2 acquired by the imaging apparatus 1A and the imaging conditions are transmitted to and stored in the image storage system 9. Note that the radiation image acquired by the imaging apparatus 1B and the imaging conditions in a case in which the radiation image is acquired are also transmitted to and stored in the image storage system 9.

The scattered ray removal unit 22 removes the scattered ray component from each of the first radiation image G1 and the second radiation image G2 acquired by the image acquisition unit 21. In the following, the removal of the scattered ray component will be described. As a method for removing the scattered ray component, for example, any method, such as a method disclosed in JP2015-043959A, can be used. In the following, scattered ray removal processing in a case in which the method disclosed in JP2015-043959A is used will be described. Note that, in the following description, G1 and G2 will be used as reference numerals for the first and second radiation images from which the scattered ray component is removed.

First, the scattered ray removal unit 22 acquires a virtual model of the subject H having an initial body thickness distribution Ts(x,y). The virtual model is data virtually representing the subject H of which a body thickness in accordance with the initial body thickness distribution Ts(x, y) is associated with a coordinate position of each pixel of the first radiation image G1. Note that the virtual model of the subject H having the initial body thickness distribution Ts(x,y) is stored in the storage 13 in advance, but the virtual model may be acquired from an external server in which the virtual model is stored.

Next, as shown in Expression (1) and Expression (2), the scattered ray removal unit 22 derives an estimated primary ray image Ip(x,y) obtained by estimating a primary ray image obtained by imaging the virtual model and an estimated scattered ray image Is(x,y) obtained by estimating a scattered ray image obtained by imaging the virtual model, based on the virtual model. Moreover, as shown in Expression (3), the scattered ray removal unit 22 derives an image obtained by combining the estimated primary ray image Ip(x,y) and the estimated scattered ray image Is(x,y) as an estimated image Im(x,y) obtained by estimating the first radiation image G1 obtained by imaging the subject H.

$$Ip(x, y) = Io(x, y) \times \exp(-\mu 1 \text{Soft} T(x, y) \times T(x, y)) \tag{1}$$

$$Is(x, y) = Ip(x, y) \times (STPR1(T(x, y)) * PSF1(T(x, y))) \tag{2}$$

$$Im(x, y) = Is(x, y) + Ip(x, y) \tag{3}$$

Here, (x,y) is a coordinate of a pixel position of the first radiation image G1, Io(x,y) is a pixel value of the first radiation image G1 at the pixel position (x,y), Ip(x,y) is the primary ray component at the pixel position (x,y), and Is(x,y) is the scattered ray component at the pixel position (x,y). Note that, in a case of deriving the first estimated image Im(x,y), the initial body thickness distribution Ts(x,y) is used as the body thickness distribution T(x,y) in Expression (1) and Expression (2).

In addition, $\mu 1$Soft(T(x,y)) in Expression (1) is an attenuation coefficient in accordance with the body thickness distribution (x,y) of the soft tissue of the human body at the pixel position (x,y). The $\mu 1$Soft(T(x,y)) need only be obtained in advance experimentally or by simulation and stored in the storage 13. In addition, the STPR1(T(x,y)) in Expression (2) is a ratio (scatter-to-primary ratio) of a scattered dose to a primary dose included in the radiation after being transmitted through the subject H having the body thickness distribution T(x,y). The STPR1(T(x,y)) need only also be obtained in advance experimentally or by simulation, and stored in the storage 13.

In addition, the PSF1(T(x,y)) in Expression (2) is a point spread function representing the distribution of the scattered rays spreading from one pixel in accordance with the body thickness distribution T(x,y), and is defined in accordance with the energy characteristic of the radiation. In addition, * is an operator representing a convolution operation. The PSF1 is also changed due to a distribution of irradiation fields in the imaging apparatus 1A, a distribution of the compositions of the subject H, the irradiation dose at the time of imaging, the tube voltage, an imaging distance, the characteristics of the radiation detectors 5 and 6, and the like. Therefore, the PSF1 need only be experimentally obtained in advance for each energy characteristic of the radiation used by the imaging apparatus 1A in accordance with irradiation field information, subject information, the imaging condition, and the like, and stored in the storage 13.

The attenuation coefficient $\mu 1$Soft, the STPR1, and the PSF1 are examples of a first characteristic related to a first imaging apparatus according to the present disclosure.

Next, the scattered ray removal unit 22 corrects the initial body thickness distribution Ts(x,y) of the virtual model such that a difference between the estimated image Im and the first radiation image G1 is small. The scattered ray removal unit 22 updates the body thickness distribution T(x,y), the scattered ray component Is(x,y), and the primary ray component Ip(x,y) by repeating the derivation of the body thickness distribution T(x,y), the scattered ray component Is(x,y), and the primary ray component Ip(x,y) until a difference between the estimated image Im and the first radiation image G1 satisfies a predetermined termination condition. The scattered ray removal unit 22 subtracts the scattered ray component Is(x,y) derived by Expression (2) from the first radiation image G1 in a case in which the termination condition is satisfied. As a result, the scattered ray component included in the first radiation image G1 is removed. Note that the body thickness distribution T(x,y) derived in a case in which the termination condition is satisfied is used for various calculations described below.

On the other hand, the scattered ray removal unit 22 also performs the scattered ray removal processing on the second radiation image G2 in the same manner as in the first radiation image G1.

In the following, the derivation of the attenuation coefficient $\mu 1$Soft and the STPR1 will be described. The attenuation coefficient $\mu 1$Soft and the STPR1 are derived by the characteristic derivation unit 27. In a case in which the attenuation coefficient $\mu 1$Soft and the STPR1 are derived, the image acquisition unit 21 acquires a standard image K0 by causing the imaging apparatus 1A to image a standard object simulating the human body. In this case, only one radiation detector is used. Note that, in a case in which the standard image K0 is stored in the image storage system 9, the image acquisition unit 21 acquires the standard image K0 from the image storage system 9. In addition, in the following description, the reference numeral "1" is omitted for generalization.

Figure 4:
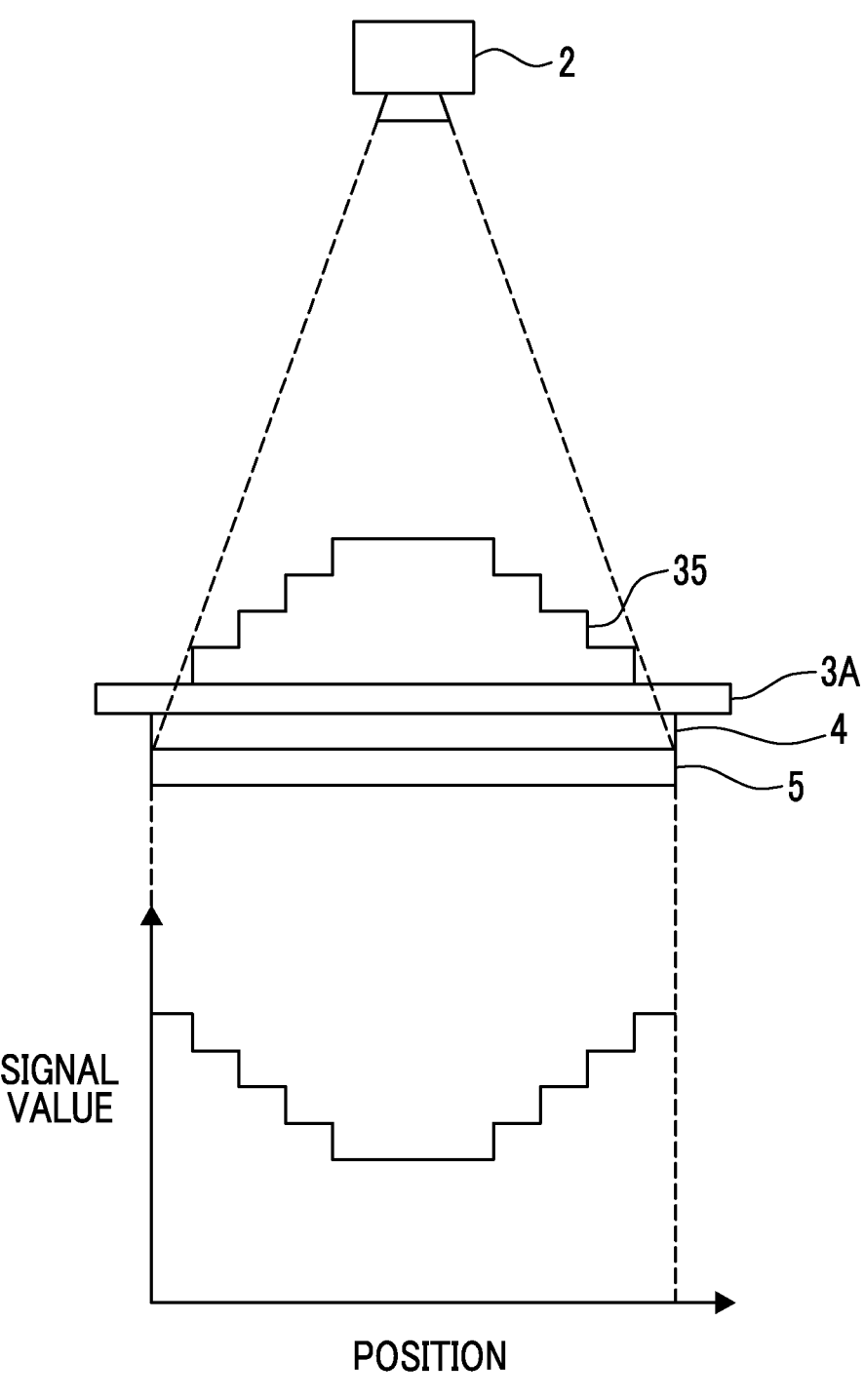
FIG. 4 is a diagram for describing imaging of a standard object.

FIG. 4 is a diagram for describing imaging of the standard object. As shown in FIG. 4, a standard object 35 is made of a material having different thickness portions, such as 5 cm, 10 cm, and 20 cm, in stages and having the same radiation transmittance as the soft tissue (fat and muscle) of the human body. Therefore, the standard object 35 simulates a radiation characteristic of the human body. Here, the soft tissue is a mixture of the muscle and the fat in a certain ratio. A mixing ratio of the muscle and the fat differs depending on gender, physique, and the like, but can be defined by an average body fat percentage (25%). Therefore, a material, such as acrylic, which corresponds to the composition mixed at a ratio of 0.75 of the muscle and 0.25 of the fat, is used as the standard object 35.

In a case of acquiring the standard image K0, as shown in FIG. 4, the standard object 35 is placed on the top plate 3A of the imaging table 3, the radiation source 2 is driven to emit the radiation to the radiation detector (here, the first radiation detector 5) via the grid 4, so that the image acquisition unit 21 acquires the standard image K0. The pixel value of each pixel of the standard image K0 includes the primary ray component based on the radiation traveling straight through the standard object 35 and the scattered ray component based on the radiation scattered by the standard object 35.

Note that the standard object 35 is not limited to one object having different thicknesses as shown in FIG. 4. A plurality of standard objects having different thicknesses may be used. In this case, the standard image K0 may be acquired by imaging the plurality of standard objects at once, or the standard images corresponding to each of the standard objects may be acquired by imaging the plurality of standard objects separately.

Also in a case of the acquisition of the standard image K0, the imaging conditions, such as the imaging dose, the tube voltage, the source image receptor distance (SID), which is a distance between the radiation source 2 and the surfaces of the first and second radiation detectors 5 and 6, and the presence or absence of the grid 4, are set.

The characteristic derivation unit 27 acquires the imaging conditions set at the time of imaging. In addition, the characteristic derivation unit 27 acquires the energy characteristic of the radiation at the time of imaging of the standard object 35 in order to derive the attenuation coefficient μSoft and the STPR. The energy characteristic of the radiation may be acquired from the imaging apparatus 1A, or the energy characteristic of the radiation may be stored in the image storage system 9 and acquired from the image storage system 9. Note that a nominal value of the imaging apparatus 1A may be used for the energy characteristic, since there are individual differences in the characteristic of the devices, it is preferable to measure the energy characteristic in advance by using a semiconductor dosimeter.

Here, the energy characteristic is defined by any one of (i) a spectrum of the radiation emitted from the radiation source 2, (ii) the tube voltage [kV] and a total filtration amount [mmAl equivalent], or (iii) the tube voltage [kV] and an aluminum half-valent layer [mmAl]. The spectrum of the radiation is obtained by plotting a relationship between the number of relative radiation photons with respect to the radiation energy [keV]. The tube voltage means the maximum value of the generated radiation energy distribution. The total filtration amount is obtained by converting the filtration amount of each constituting component which configures the imaging apparatus 1A, such as a radiation generator and a collimator, in the radiation source 2 into a thickness of the aluminum. The influence of the beam hardening in the imaging apparatus 1A is larger and the total amount of high-energy components in the wavelength distribution of the radiation is larger as the total filtration amount is larger. The half-value layer is defined by the thickness of the aluminum necessary to attenuate the dose in half with respect to the generated radiation energy distribution. The high-energy components in the wavelength distribution of the radiation are larger as the aluminum in the half-value layer is thicker.

Figure 5:
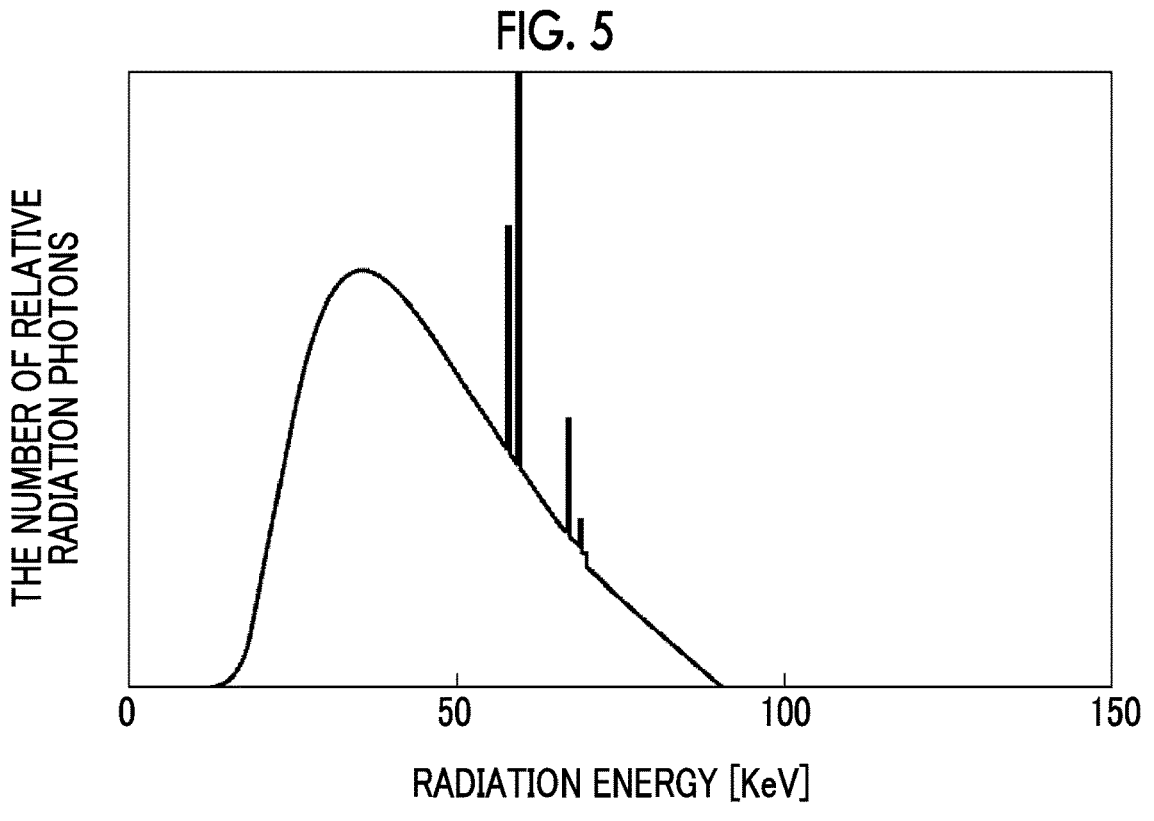
FIG. 5 is a diagram showing a spectrum of radiation.

FIG. 5 is a diagram showing the spectrum of the radiation. In FIG. 5, the spectrum corresponds to the tube voltage of 90 kV and the total filtration amount of 2.5 mmAl. Note that the total filtration amount of 2.5 mmAl corresponds to the half-value layer 2.96 mmAl.

By using the energy characteristic of the radiation, the characteristic derivation unit 27 derives a relationship between the thickness of the standard object 35 and the radiation attenuation coefficient of the standard object 35, which reflects the influence of the beam hardening of the object present between the standard object 35 and the radiation detector 5.

The characteristic derivation unit 27 first derives the energy spectrum of the radiation from the acquired energy characteristic of the radiation by using a well-known Tucker approximation formula or the like. Note that the acquired energy characteristic is the energy spectrum of the radiation, the acquired energy spectrum need only be used as it is.

Moreover, the characteristic derivation unit 27 derives the radiation attenuation coefficient depending on the thickness of the standard object 35 by simulating the spectrum of the radiation by using a radiation attenuation characteristic of the soft tissue of the human body.

Figure 6:
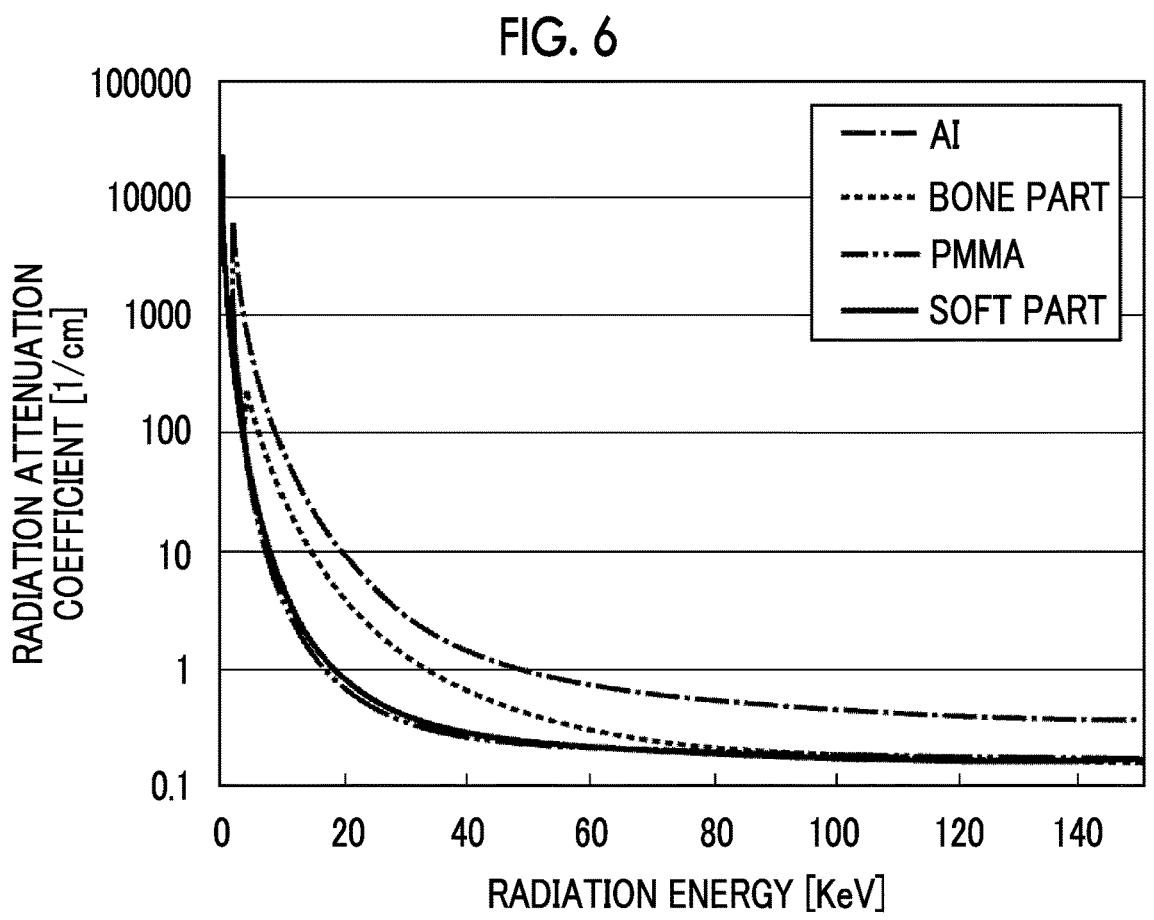
FIG. 6 is a diagram showing radiation attenuation coefficients of a soft tissue, a bone tissue, and aluminum of a human body with respect to radiation energy.

Here, in a case in which the energy spectrum of the radiation emitted from the radiation source 2 is defined as Sin(E) and the thickness of the standard object 35 is defined as t, the radiation dose Xbody(t) after being transmitted through the standard object 35 can be calculated by Expression (4) using a radiation attenuation coefficient μSoft(E) of the soft tissue of the human body. Note that the radiation attenuation coefficients of the soft tissue, the bone tissue, and the aluminum of the human body with respect to the radiation energy are known as shown in FIG. 6. The aluminum is the interspace material for the grid 4. Here, FIG. 6 also shows the radiation attenuation coefficient of the acrylic (polymethyl methacrylate, PMMA), which is the material of the standard object 35. The radiation attenuation coefficient of the acrylic substantially matches the radiation attenuation coefficient of the soft tissue of the human body, as shown in FIG. 6.

$$X_{body}(t) = \int_0^\infty S_{in}(E) \times \exp\{-\mu_{Soft}(E) \times t\} dE \tag{4}$$

On the other hand, in a case in which the standard object 35 is imaged by the imaging apparatus 1A, the top plate 3A and the grid 4 are present between the standard object 35 and the radiation detectors 5 and 6. A material of the top plate 3A is the acrylic and the interspace material of the grid 4 is the aluminum. In a case in which the radiation attenuation coefficient of the acrylic is defined as μPMMA(E), the thickness of the top plate 3A (that is, the thickness of the acrylic) is defined as tPMMA, the radiation attenuation characteristic of the aluminum is defined as μAl(E), and the thickness of grid 4 (that is, the aluminum) is defined as tAl, an X-ray dose Xout(t) after being transmitted through the top plate 3A and the grid 4 is represented by Expression (5).

$$X_{out}(t) = \int_0^\infty S_{in}(E) \times \exp\{-\mu_{Soft}(E) \times t\} \times \qquad (5)$$

$$\exp\{-\mu_{PMMA}(E) \times t_{PMMA}\} \times \exp\{-\mu_{Al}(E) \times t_{Al}\}dE$$

Note that, in a case in which the material of the top plate 3A and the interspace material of the grid 4 are unknown, the X-ray dose Xout(t) after being transmitted through the top plate 3A and the grid 4 cannot be derived by Expression (5). In this case, the energy characteristic (kV, TF0) of the radiation emitted from the radiation source 2 and the energy characteristic (kV, TF1) of the radiation after being transmitted through the top plate 3A and the grid 4 are measured using a dosimeter, and the X-ray dose Xout(t) after being transmitted through the top plate 3A and the grid 4 can be derived by Expression (5-1) using the energy characteristic (kV, TF0) and the energy characteristic (kV, TF1). Note that the energy characteristic in Expression (5-1) represents the total filtration amount (mmAl equivalent) of the radiation emitted by a certain tube voltage [kV].

$$X_{out}(t) = \qquad (5-1)$$
$$\int_0^\infty S_{in}(E) \times \exp\{-\mu_{Soft}(E) \times t\} \times \exp\{-\mu_{Al}(E) \times (TF1 - TF0)\}dE$$

The radiation attenuation coefficient of the standard object 35 in the imaging system including the top plate 3A and the grid 4 is obtained by representing an attenuation ratio of the radiation after being transmitted through the standard object 35 by an attenuation index as shown in Expression (6) with reference to the radiation dose in a case in which the standard object 35 is not present (that is, in a case in which the thickness of the standard object 35 is 0).

$$\frac{X_{out}(t)}{X_{out}(0)} = \exp\{-\mu_{Soft}(t) \times t\} \qquad (6)$$

By solving Expression (6) with respect to the radiation attenuation coefficient μSoft(t) of the soft tissue as shown in Expression (7), a relationship between a thickness t of the standard object 35 and the radiation attenuation coefficient can be derived.

$$\mu_{Soft}(t) = -\frac{\ln\left\{\frac{X_{out}(t)}{X_{out}(0)}\right\}}{t} \qquad (7)$$

Figure 7:
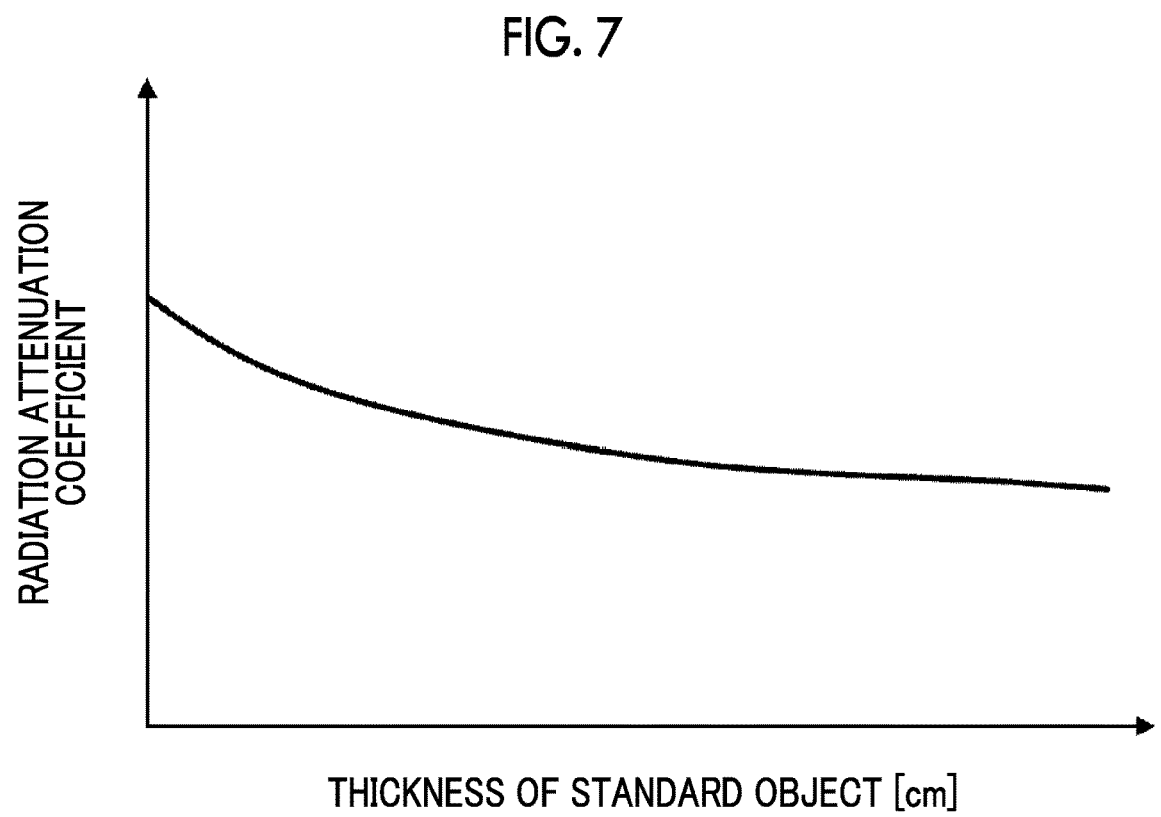
FIG. 7 is a diagram showing a relationship between a thickness of the standard object and the radiation attenuation coefficient.

The standard object 35 has a plurality of different thicknesses in stages. Therefore, the characteristic derivation unit 27 derives the radiation attenuation coefficient by Expression (7) for each of the plurality of thicknesses of the standard object 35. Moreover, the characteristic derivation unit 27 derives the relationship between the thickness t of the standard object 35 and the radiation attenuation coefficient by performing an interpolation calculation using the radiation attenuation coefficient of the thickness present in the standard object 35 for the radiation attenuation coefficient of the thickness that is not present in the standard object 35. FIG. 7 is a diagram showing a relationship between the thickness t of the standard object 35 and the radiation attenuation coefficient. FIG. 7 shows the relationship between the thickness of the standard object 35 and the radiation attenuation coefficient in a case in which the tube voltage is 90 kV and the total filtration amount is 2.5 mmAl. The characteristic derivation unit 27 derives the relationship between the thickness of the standard object 35 and the radiation attenuation coefficient for each energy characteristic of the radiation, and stores the derived relationship in the storage 13.

The characteristic derivation unit 27 derives the radiation attenuation coefficient corresponding to the thickness of the standard object 35 based on the relationship between the thickness of the standard object 35 and the derived radiation attenuation coefficient. Moreover, the primary ray component included in the standard image K0 is derived based on the radiation attenuation coefficient corresponding to the thickness of the standard object 35.

Here, in a case in which the pixel value of each pixel of the standard image K0 is defined as I0o(x,y), the thickness of the standard object 35 corresponding to each pixel of the standard image K0 is defined as T0(x,y), and the radiation attenuation coefficient derived by Expression (7) with respect to the thickness T0(x,y) of each pixel of the standard image K0 is defined as μSoft0(x,y), the characteristic derivation unit 27 derives a primary ray component I0p(x,y) included in the pixel value of each pixel of the standard image K0 by Expression (8). Note that since the standard object 35 has the plurality of thicknesses in stages, the characteristic derivation unit 27 derives the primary ray component I0p(x,y) for each thickness present in the standard object 35. Note that the characteristic derivation unit 27 may derive the relationship between the thickness of the standard object 35 and the primary ray component by performing the interpolation calculation using the primary ray component of the thickness that is present in the standard object 35 for the primary ray component corresponding to the thickness that is not present in the standard object 35.

$$I0p(x,y)=I0o(x,y)\times\exp(-\mu Soft0(x,y)\times T0(x,y)) \qquad (8)$$

In addition, the characteristic derivation unit 27 derives the scattered ray component included in the standard object 35 based on the difference between the pixel value of the standard image K0 and the primary ray component. That is, the characteristic derivation unit 27 derives a scattered ray component I0s(x,y) by Expression (9). Note that since the standard object 35 has the plurality of thicknesses in stages, the scattered ray component I0s(x,y) corresponding to the stepwise thickness of the standard object 35 is derived. Note that the characteristic derivation unit 27 need only derive the relationship between the thickness of the standard object 35 and the scattered ray component by performing the interpolation calculation using the scattered ray component of the thickness that is present in the standard object 35 for the scattered ray component corresponding to the thickness that is not present in the standard object 35.

$$I0s(x,y)=I0o(x,y)-I0p(x,y) \qquad (9)$$

The characteristic derivation unit 27 derives a ratio of the scattered ray component I0s(x,y) to the primary ray component I0p(x,y) (that is, I0s(x,y)/I0p(x,y)) for each thickness of the standard object 35 as the STPR. Note that since the thicknesses of the standard object 35 are different in stages, the STPR at the thickness that is not present at the standard object 35 need only be derived by the interpolation calculation using the STPR at the thickness that is present in the standard object 35.

Figure 8:
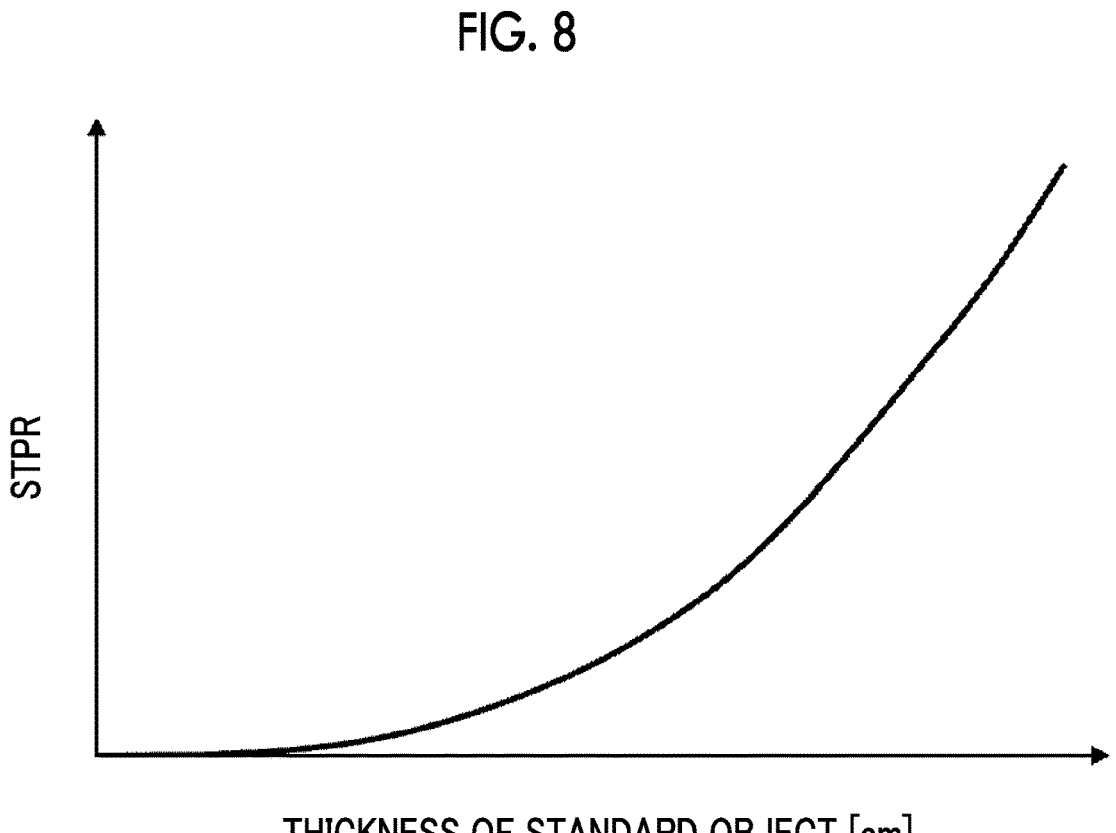
FIG. 8 shows a scattered ray model.

FIG. 8 is a diagram showing a relationship between the thickness of the standard object and the STPR. FIG. 8 shows a relationship between the thickness of the standard object 35 and the STPR in a case in which the tube voltage is 90 kV and the total filtration amount is 2.5 mmAl. The characteristic derivation unit 27 stores the derived scattered ray model in the storage 13. Note that the standard object 35 simulates the radiation characteristic of the human body. Therefore, the relationship between the thickness of the standard object and the STPR shown in FIG. 8 represents a relationship between the thickness of the subject H and the STPR.

Note that the relationship between the thickness of the standard object and STPR need only be derived for each energy characteristic of the radiation that can be emitted by the radiation source 2 of the imaging apparatus 1A and stored in the storage 13.

Here, in the present embodiment, in addition to the radiation attenuation coefficient of the soft tissue, a radiation attenuation coefficient of the bone tissue is also used. Therefore, the characteristic derivation unit 27 also derives the radiation attenuation coefficient of the bone tissue. In the following, the derivation of a radiation attenuation coefficient $\mu$1Bone of the bone tissue will be described. Note that the radiation attenuation coefficient $\mu$1Bone of the bone tissue is also an example of a first characteristic according to the present disclosure. In addition, in the following description, the reference numeral "1" is omitted for generalization.

Here, a state is assumed in which the soft tissue and the bone tissue overlap on a radiation transmission path, and in a case in which the thickness of the soft tissue is defined as tSoft, the radiation attenuation coefficient can be derived as a function depending on the thickness of the soft tissue. In a case in which the energy spectrum of the radiation emitted from the radiation source 2 is defined as Sin(E) and the thickness of the soft tissue of the subject H is defined as tSoft, a radiation dose Xout1(tSoft) after being transmitted through the subject H in a case in which the bone tissue is not present can be calculated by Expression (10) for each thickness t of the subject H using the radiation attenuation coefficient $\mu$Soft(E) of the soft tissue of the human body. Note that, in Expression (10), as in Expression (5), the radiation attenuation coefficient of the object (that is, the top plate 3A and the grid 4) that is present between the subject H and the radiation detectors 5 and 6 is taken into consideration.

$$X_{out1}(t) = \int_0^\infty S_{in}(E) \times \exp\{-\mu_{Soft}(E) \times t_{Soft}\} \times$$
$$\exp\{-\mu_{PMMA}(E) \times t_{PMMA}\} \times \exp\{-\mu_{Al}(E) \times t_{Ai}\}dE \quad (10)$$

A radiation dose Xout2(t) in a case in which the bone tissue is present is derived by Expression (11) further using a radiation attenuation coefficient $\mu$Bone(E) of the bone tissue.

$$X_{out2}(t) = \int_0^\infty S_{in}(E) \times \exp\{-\mu_{Soft}(E) \times t_{Soft} - \mu_{Bone}(E) \times t_{Bone}\} \times$$
$$\exp\{-\mu_{PMMA}(E) \times t_{PMMA}\} \times \exp\{-\mu_{Al}(E) \times t_{Ai}\}dE \quad (11)$$

The radiation attenuation coefficient of the bone tissue is obtained by representing an attenuation ratio of the radiation dose due to the bone tissue by the attenuation index with reference to the radiation dose in a case in which the bone tissue is not present, as shown in Expression (12).

$$\frac{X_{out2}(t)}{X_{out1}(t)} = \exp\{-\mu_{Bone}(t) \times t_{Bone}\} \quad (12)$$

By solving Expression (12) for $\mu$Bone(t) as shown in Expression (13), the relationship between the thickness t of the subject H and the radiation attenuation coefficient of the bone tissue can be derived. Note that tBone is the thickness of the bone tissue.

$$\mu_{Bone}(t) = -\frac{\ln\left\{\frac{X_{out2}(t)}{X_{out1}(t)}\right\}}{t_{Bone}} \quad (13)$$

Note that the PSF is, as described above, also changed due to a distribution of irradiation fields in the imaging apparatus 1A, a distribution of the compositions of the subject H, the irradiation dose at the time of imaging, the tube voltage, an imaging distance, the characteristics of the radiation detectors 5 and 6, and the like. Therefore, the characteristic derivation unit 27 need only experimentally obtain PSF in advance for each energy characteristic of the radiation used by the imaging apparatus 1A in accordance with irradiation field information, subject information, the imaging conditions, and the like, and store the obtained PSF in the storage 13.

Here, in the present embodiment, the characteristic derivation unit 27 derives a radiation attenuation coefficient $\mu$2Soft of the soft tissue, a radiation attenuation coefficient $\mu$2Bone of the bone tissue, the STPR2, and the PSF2 for the imaging apparatus 1B in the same manner as described above. The derived soft tissue radiation attenuation coefficient $\mu$2Soft, bone tissue radiation attenuation coefficient $\mu$2Bone, STPR2, and PSF2 need only be stored in the storage 13. Even for the imaging apparatus 1B, the radiation attenuation coefficient $\mu$2Soft of the soft tissue, the radiation attenuation coefficient $\mu$2Bone of the bone tissue, the STPR2, and the PSF2 are examples of a second characteristic related to a second imaging apparatus according to the present disclosure.

The subtraction unit 23 performs energy subtraction processing to derive a bone part image Gb in which a bone part of the subject H is extracted and a soft part image Gs in which a soft part is extracted from the first and second radiation images G1 and G2, which are subjected to the scattered ray removal processing. The bone part image Gb and the soft part image Gs are examples of a first bone part image and a first soft part image according to the present disclosure. Note that the first and second radiation images G1 and G2 in the subsequent processing are processed radiation images from which the scattered ray component is removed.

In a case in which the bone part image Gb is derived, the subtraction unit 23 performs weighting subtraction between the corresponding pixels with respect to the first and second radiation images G1 and G2 as shown in Expression (14) to generate the bone part image Gb in which the bone part of the subject H included in each of the radiation images G1 and G2 is extracted. In Expression (14), $\alpha$1 is a weighting coefficient, and is set as a value capable of extracting the bone part of the subject H included in each of the radiation images G1 and G2 by Expression (14) based on the radiation attenuation coefficients of the bone tissue and the soft tissue.

$$Gb(x,y) = G1(x,y) - \alpha 1 \times G2(x,y) \quad (14)$$

On the other hand, in a case in which the soft part image Gs is derived, the subtraction unit 23 performs weighting subtraction between the corresponding pixels with respect to the first and second radiation images G1 and G2 as shown in Expression (15) to generate the soft part image Gs in which the soft part of the subject H included in each of the radiation images G1 and G2 is extracted. In Expression (15), α2 is a weighting coefficient, and is set as a value capable of extracting the soft part of the subject H included in each of the radiation images G1 and G2 by Expression (15) based on the radiation attenuation coefficients of the bone tissue and the soft tissue.

$$Gs(x,y)=G1(x,y)-\alpha2\times G2(x,y) \tag{15}$$

Figure 9:
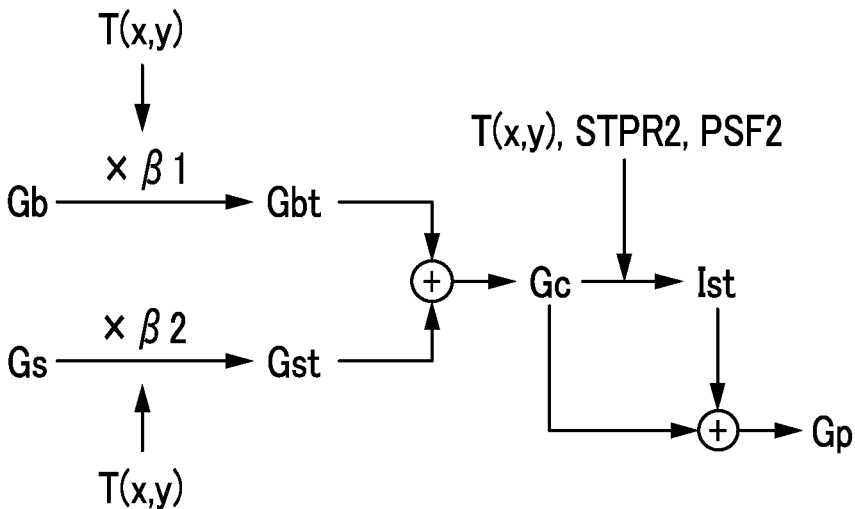
FIG. 9 is a diagram schematically showing processing performed by a conversion unit and a derivation unit.

Next, processing performed by the conversion unit 24 and the derivation unit 25 will be described. FIG. 9 is a diagram schematically showing the processing performed by the conversion unit 24 and the derivation unit 25. First, the processing performed by the conversion unit 24 will be described.

Since the bone part image Gb and the soft part image Gs derived by the subtraction unit 23 are derived from the first and second radiation images G1 and G2 acquired by the imaging apparatus 1A, the bone part image Gb and the soft part image Gs have the contrast based on the first characteristic related to the imaging apparatus 1A (that is, radiation energy, radiation attenuation coefficient, STPR1, and PSF1). The conversion unit 24 converts the bone part image Gb and the soft part image Gs such that the bone part image Gb and the soft part image Gs derived by the subtraction unit 23 have the contrast based on the second characteristic related to the imaging apparatus 1B.

Regarding the bone part image Gb, the conversion unit 24 converts the contrast of the bone part image Gb by Expression (16) to derive a converted bone part image Gbt. In addition, regarding the soft part image Gs, the conversion unit 24 converts the contrast of the soft part image Gs by Expression (17) to derive a converted soft part image Gst. Note that β1 in Expression (16) is derived by β1=μ2Soft(T(x,y))/μ1Soft(T(x,y)), and β2 in Expression (17) is derived by β2=μ2Bone(T(x,y))/μ1Bone(T(x,y)). Note that the body thickness distribution T(x,y) derived by the scattered ray removal unit 22 is used. The converted bone part image Gbt and the converted soft part image Gst are examples of a second bone part image and a second soft part image according to the present disclosure.

$$Gbt(x, y) = \beta1 \times Gb(x, y) \tag{16}$$

$$Gst(x, y) = \beta2 \times Gs(x, y) \tag{17}$$

The derivation unit 25 derives a composite radiation image Gc by adding the converted bone part image Gbt and the converted soft part image Gst derived by the conversion unit 24 between corresponding pixels. The composite radiation image Gc is an example of a processed radiation image according to the present disclosure.

Here, since the bone part image Gb and the soft part image Gs are derived from the first and second radiation images G1 and G2 from which the scattered ray component is removed, the converted bone part image Gbt, the converted soft part image Gst, and the composite radiation image Gc do not include the scattered ray component. Therefore, the composite radiation image Gc may be used as it is for the comparative interpretation between the first and second radiation images G1 and G2 or the bone part image Gb and the soft part image Gs, but the scattered ray component in accordance with the second characteristic is added to the composite radiation image Gc in the present embodiment.

Therefore, the derivation unit 25 uses the second characteristic derived by the characteristic derivation unit 27 for the imaging apparatus 1B, that is, the STPR2 and the PSF2, to derive a scattered ray image Isc representing the scattered ray component in accordance with the second characteristic by Expression (18). The scattered ray component in accordance with the second characteristic is the scattered ray component in accordance with the scattered ray component included in the radiation image acquired in a case in which the subject H is imaged by the imaging apparatus 1B. Note that in Expression (18), Gc(x,y) is the pixel value of each pixel in the composite radiation image Gc. In addition, the body thickness distribution T(x,y) derived by the scattered ray removal unit 22 is used.

$$Isc(x,y)=Gc(x,y)\times STPR2(T(x,y))*PSF2(T(x,y)) \tag{18}$$

Moreover, the derivation unit 25 derives a processed radiation image Gp by adding corresponding pixels of the composite radiation image Ge and the scattered ray image Isc.

Figure 10:
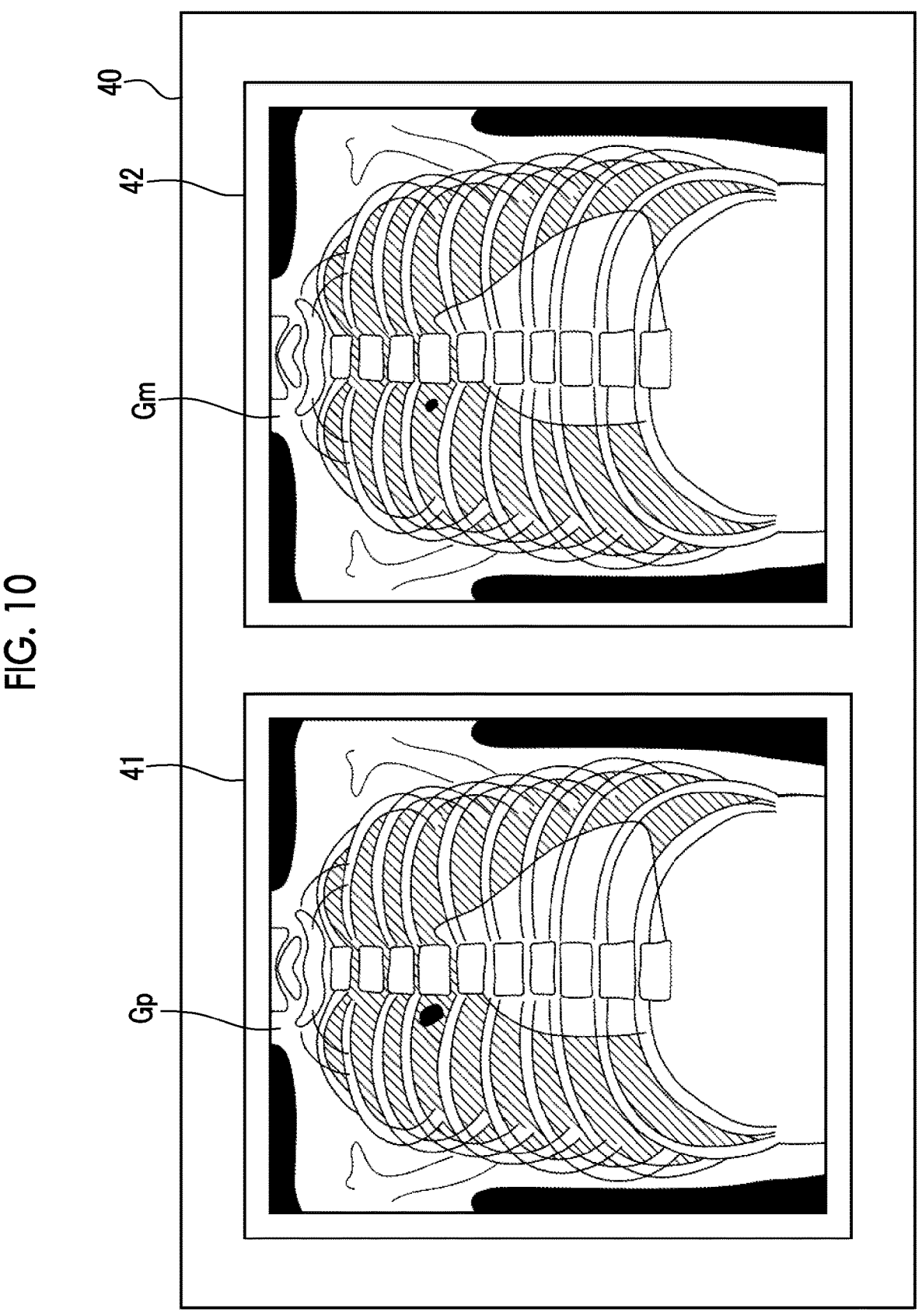
FIG. 10 is a diagram showing an interpretation screen.

The display controller 26 displays an interpretation screen on the display 14. FIG. 10 is a diagram showing the interpretation screen. As shown in FIG. 10, an interpretation screen 40 has a first display region 41 for displaying the radiation image of the latest examination and a second display region 42 for displaying the past radiation image. The processed radiation image Gp acquired by the imaging apparatus 1A and derived by the radiation image processing device 10 according to the present embodiment is displayed in the first display region. A past radiation image Gm acquired from the image storage system 9 is displayed in the second display region.

Figure 11:
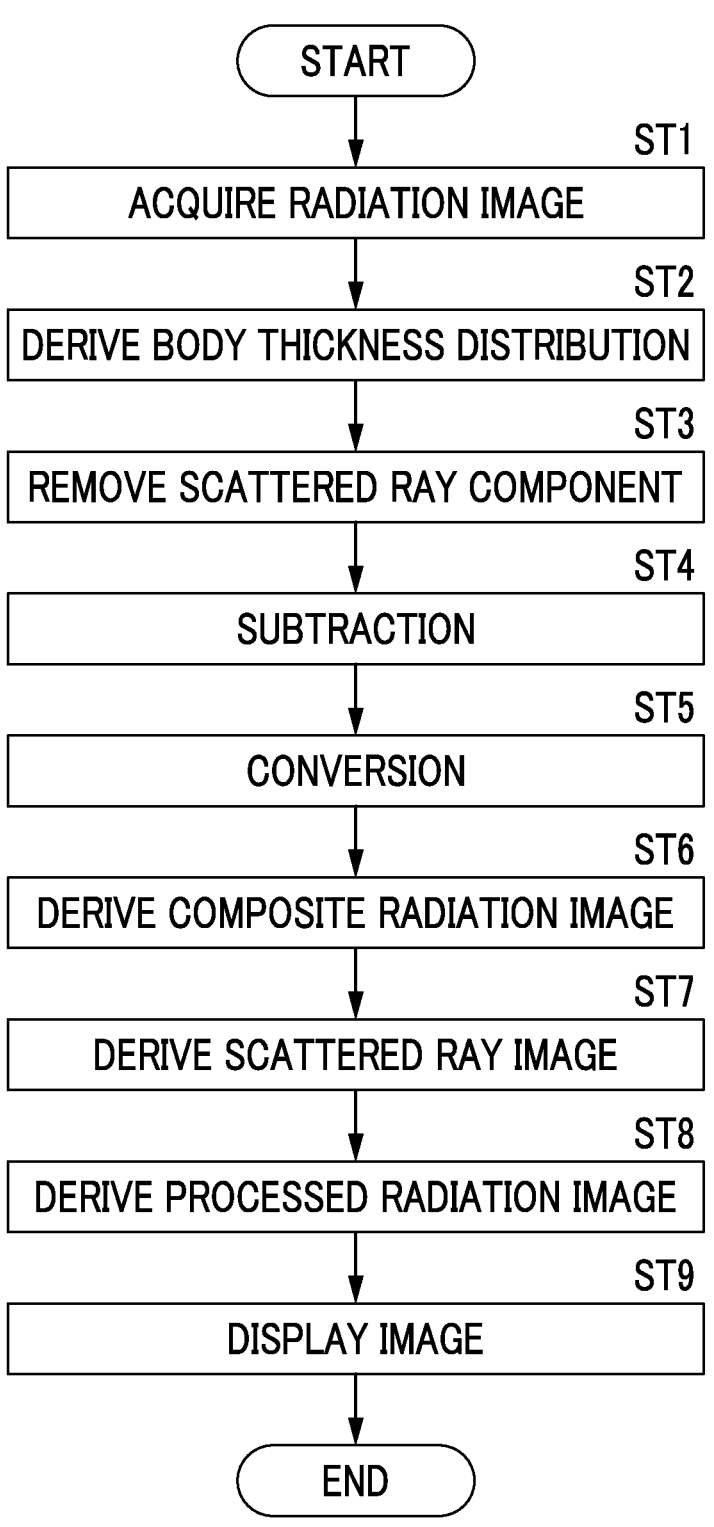
FIG. 11 is a flowchart showing processing performed in the present embodiment.

Then, processing performed in the present embodiment will be described. FIG. 11 is a flowchart showing processing performed in the present embodiment. Note that the first and second radiation images G1 and G2 are acquired by the imaging apparatus 1A and stored in the storage 13. In addition, the first characteristic and the second characteristic are acquired by the characteristic derivation unit 27 and stored in the storage 13. In a case in which an instruction for starting the processing is input from the input device 15, the image acquisition unit 21 acquires the first and second radiation images G1 and G2 from the storage 13 (radiation image acquisition; step ST1). Then, the scattered ray removal unit 22 derives the body thickness distribution of the subject H from the first and second radiation images G1 and G2 (step ST2), and removes the scattered ray component from each of the first and second radiation images G1 and G2 (step ST3).

Then, the subtraction unit 23 derives the bone part image Gb in which the bone part of the subject H is extracted and the soft part image Gs in which the soft part is extracted from the first and second radiation images G1 and G2 from which the scattered ray component is removed (subtraction; step ST4).

Subsequently, the conversion unit 24 converts the contrasts of the bone part image Gb and the soft part image Gs to derive the converted bone part image Gbt and the converted soft part image Gst (conversion; step ST5). Then, the derivation unit 25 derives the composite radiation image Gc by adding the converted bone part image Gbt and the converted soft part image Gst derived by the conversion unit 24 (step ST6). In addition, the derivation unit 25 also derives the scattered ray image Isc representing the scattered ray component in accordance with the second characteristic (step ST7). Moreover, the derivation unit 25 derives the processed radiation image Gp by adding the composite radiation image Gc and the scattered ray image Isc (step ST8). Further, the display controller 26 displays the processed radiation image Gp and the past radiation image Gm on the display 14 (image display; step ST9), and terminates the processing.

Here, the radiation image acquired by the imaging apparatus 1A includes the scattered ray components in accordance with the characteristics, such as the energy of the radiation used in the imaging apparatus 1A, the top plate of the imaging table on which the subject H is placed in the imaging apparatus 1A, the scattered ray removal grid for removing the scattered ray component included in the radiation transmitted through the subject H in the imaging apparatus 1A, and the like. Therefore, the radiation image acquired by the imaging apparatus 1A has the contrast in accordance with the first characteristic of the imaging apparatus 1A.

On the other hand, the radiation image acquired by the imaging apparatus 1B includes the scattered ray components in accordance with the characteristics, such as the energy of the radiation used in the imaging apparatus 1B, the top plate of the imaging table on which the subject H is placed in the imaging apparatus 1B, the scattered ray removal grid for removing the scattered ray component included in the radiation transmitted through the subject H in the imaging apparatus 1B, and the like. Therefore, the radiation image acquired by the imaging apparatus 1B has the contrast in accordance with the second characteristic related to the imaging apparatus 1B.

In the present embodiment, the scattered ray component is removed from the first and second radiation images G1 and G2 acquired by the imaging apparatus 1A, and the bone part image Gb and the soft part image Gs are derived from the first and second radiation images G1 and G2 from which the scattered ray component is removed. Further, based on the first characteristic, the second characteristic, and the body thickness distribution T(x,y) of the subject H, the bone part image Gb and the soft part image Gs are converted to have the contrast based on the second characteristic related to the imaging apparatus 1B, and the converted bone part image Gbt and the converted soft part image Gst are combined to derive the composite radiation image Gc. Therefore, in the present embodiment, the radiation image acquired by the imaging apparatus 1A can be converted to have the contrast corresponding to that of the radiation image acquired by the imaging apparatus 1B. As a result, even in a case in which the radiation images used for the comparative interpretation are acquired by different imaging apparatuses 1A and 1B, the contrast between the radiation images can be matched. Therefore, according to the present embodiment, the comparative interpretation can be performed with high accuracy.

In addition, based on the second characteristic and the body thickness distribution, the scattered ray image representing the scattered ray component in accordance with the second characteristic is derived, and the processed radiation image Gp is derived by using the derived scattered ray image to make it possible to match the contrasts of the radiation images acquired by different imaging apparatuses 1A and 1B, also including the scattered ray component.

Note that, in each embodiment described above, the first and second radiation images G1 and G2 are acquired by the one-shot method in a case in which the energy subtraction processing is performed, but the present disclosure is not limited to this. The first and second radiation images G1 and G2 may be acquired by a so-called two-shot method in which imaging is performed twice by using only one radiation detector. In a case of the two-shot method, a position of the subject H included in the first radiation image G1 and the second radiation image G2 may shift due to a body movement of the subject H. Therefore, in the first radiation image G1 and the second radiation image G2, it is preferable to perform the processing according to the present embodiment after registration of the subject is performed.

In addition, in the embodiment described above, bone disease prediction processing is performed by using the radiation image acquired by the system that images the first and second radiation images G1 and G2 of the subject H by using the first and second radiation detectors 5 and 6, it is needless to say that the technology of the present disclosure can be applied to even in a case in which the first and second radiation images G1 and G2 are acquired by using an accumulative phosphor sheet instead of the radiation detector. In this case, the first and second radiation images G1 and G2 need only be acquired by stacking two accumulative phosphor sheets, emitting the radiation transmitted through the subject H, accumulating and recording radiation image information of the subject H in each of the accumulative phosphor sheets, and photoelectrically reading the radiation image information from each of the accumulative phosphor sheets. Note that the two-shot method may also be used in a case in which the first and second radiation images G1 and G2 are acquired by using the accumulative phosphor sheet.

In addition, the radiation in the embodiment described above is not particularly limited, and $\alpha$-rays or $\gamma$-rays can be used in addition to X-rays.

In addition, in the embodiment described above, various processors shown below can be used as the hardware structures of processing units that execute various pieces of processing, such as the image acquisition unit 21, the scattered ray removal unit 22, the subtraction unit 23, the conversion unit 24, the derivation unit 25, the display controller 26, and the characteristic derivation unit 27. As described above, the various processors include, in addition to the CPU that is a general-purpose processor which executes software (program) and functions as various processing units, a programmable logic device (PLD) that is a processor whose circuit configuration can be changed after manufacture, such as a field programmable gate array (FPGA), and a dedicated electric circuit that is a processor having a circuit configuration which is designed for exclusive use in order to execute a specific processing, such as an application specific integrated circuit (ASIC).

One processing unit may be configured by one of these various processors, or may be configured by a combination of two or more processors of the same type or different types (for example, a combination of a plurality of FPGAs or a combination of the CPU and the FPGA). In addition, a plurality of the processing units may be configured by one processor.

As an example of configuring the plurality of processing units by one processor, first, as represented by a computer of a client, a server, and the like there is an aspect in which one processor is configured by a combination of one or more CPUs and software and this processor functions as a plurality of processing units. Second, as represented by a system on chip (SoC) or the like, there is an aspect of using a processor that realizes the function of the entire system including the plurality of processing units by one integrated circuit (IC) chip. In this way, as the hardware structure, the various processing units are configured by using one or more of the various processors described above.

Moreover, as the hardware structures of these various processors, more specifically, it is possible to use an electrical circuit (circuitry) in which circuit elements, such as semiconductor elements, are combined.

What is claimed is:

1. A radiation image processing device comprising:
at least one processor,
wherein the processor
acquires two radiation images having a contrast based on a first characteristic related to a first imaging apparatus, the two radiation images being acquired by imaging a subject including a soft part and a bone part with the first imaging apparatus using radiation having different energy distributions,
derives a body thickness distribution of the subject based on at least one of the two radiation images,
removes a scattered ray component, which is included in radiation transmitted through the subject and is scattered by the subject, from the two radiation images based on the first characteristic,
derives a first bone part image representing a bone tissue of the subject and a first soft part image representing a soft tissue of the subject by performing weighting subtraction on the two radiation images from which the scattered ray component is removed,
converts the first bone part image and the first soft part image into a second bone part image and a second soft part image having a contrast based on a second characteristic related to a second imaging apparatus different from the first imaging apparatus, by calculating a correction factor based on a radiation attenuation coefficient included in the first characteristic, a radiation attenuation coefficient included in the second characteristic, and the body thickness distribution, and performing a calculation in which the correction factor is multiplied, for each pixel, by the first bone part image and the first soft part image, and
derives a processed radiation image having the contrast based on the second characteristic by adding all corresponding pixels of the second bone part image and the second soft part image.

2. The radiation image processing device according to claim 1,
wherein the processor
derives a scattered ray component in accordance with the second characteristic based on the second characteristic and the body thickness distribution, and further derives the processed radiation image by using the derived scattered ray component.

3. The radiation image processing device according to claim 1,
wherein the first characteristic includes energy of the radiation used in the first imaging apparatus, a radiation attenuation coefficient in accordance with the body thickness distribution for an object interposed between the subject and a radiation detector that detects the radiation transmitted through the subject in the first imaging apparatus, a ratio of the scattered ray component included in the radiation transmitted through the subject in accordance with the body thickness distribution, and a point spread function in accordance with the body thickness distribution, and
the second characteristic includes energy of the radiation used in the second imaging apparatus, a radiation attenuation coefficient in accordance with the body thickness distribution for an object interposed between the subject and a radiation detector that detects the radiation transmitted through the subject in the second imaging apparatus, a ratio of the scattered ray component included in the radiation transmitted through the subject in accordance with the body thickness distribution, and a point spread function in accordance with the body thickness distribution.

4. The radiation image processing device according to claim 1,
wherein the processor displays the processed radiation image and a radiation image of the subject acquired by the second imaging apparatus.

5. A radiation image processing method comprising:
acquiring two radiation images having a contrast based on a first characteristic related to a first imaging apparatus, the two radiation images being acquired by imaging a subject including a soft part and a bone part with the first imaging apparatus using radiation having different energy distributions;
deriving a body thickness distribution of the subject based on at least one of the two radiation images;
removing a scattered ray component, which is included in radiation transmitted through the subject and is scattered by the subject, from the two radiation images based on the first characteristic;
deriving a first bone part image representing a bone tissue of the subject and a first soft part image representing a soft tissue of the subject by performing weighting subtraction on the two radiation images from which the scattered ray component is removed;
converting the first bone part image and the first soft part image into a second bone part image and a second soft part image having a contrast based on a second characteristic related to a second imaging apparatus different from the first imaging apparatus, by calculating a correction factor based on a radiation attenuation coefficient included in the first characteristic, a radiation attenuation coefficient included in the second characteristic, and the body thickness distribution, and performing a calculation in which the correction factor is multiplied, for each pixel, by the first bone part image and the first soft part image; and
deriving a processed radiation image having the contrast based on the second characteristic by adding all corresponding pixels of the second bone part image and the second soft part image.

6. A non-transitory computer-readable storage medium that stores radiation image processing program causing a computer to execute:
a procedure of acquiring two radiation images having a contrast based on a first characteristic related to a first imaging apparatus, the two radiation images being acquired by imaging a subject including a soft part and a bone part with the first imaging apparatus using radiation having different energy distributions;
a procedure of deriving a body thickness distribution of the subject based on at least one of the two radiation images;
a procedure of removing a scattered ray component, which is included in radiation transmitted through the subject and is scattered by the subject, from the two radiation images based on the first characteristic;
a procedure of deriving a first bone part image representing a bone tissue of the subject and a first soft part image representing a soft tissue of the subject by performing weighting subtraction on the two radiation images from which the scattered ray component is removed;

a procedure of converting the first bone part image and the first soft part image into a second bone part image and a second soft part image having a contrast based on a second characteristic related to a second imaging apparatus different from the first imaging apparatus, by calculating a correction factor based on a radiation attenuation coefficient included in the first characteristic, a radiation attenuation coefficient included in the second characteristic, and the body thickness distribution, and performing a calculation in which the correction factor is multiplied, for each pixel, by the first bone part image and the first soft part image; and a procedure of deriving a processed radiation image having the contrast based on the second characteristic by adding all corresponding pixels of the second bone part image and the second soft part image.

* * * * *